US008606527B2

(12) United States Patent
Houser

(10) Patent No.: US 8,606,527 B2
(45) Date of Patent: Dec. 10, 2013

(54) SNP DETECTION BY MELT CURVE CLUSTERING

(75) Inventor: Thomas Houser, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 795 days.

(21) Appl. No.: 12/713,076

(22) Filed: Feb. 25, 2010

(65) Prior Publication Data

US 2010/0250145 A1    Sep. 30, 2010

Related U.S. Application Data

(60) Provisional application No. 61/156,034, filed on Feb. 27, 2009.

(51) Int. Cl.
*G06F 7/00* (2006.01)

(52) U.S. Cl.
USPC ............... 702/19; 702/20; 703/11; 707/700

(58) Field of Classification Search
None
See application file for complete search history.

(56) References Cited

U.S. PATENT DOCUMENTS

| 6,174,670 | B1 | 1/2001 | Wittwer |
| 2003/0104438 | A1 | 6/2003 | Eyre et al. |
| 2003/0224434 | A1 | 12/2003 | Wittwer et al. |
| 2004/0185452 | A1 | 9/2004 | Chen et al. |
| 2005/0053950 | A1 | 3/2005 | Zudaire et al. |
| 2009/0037117 | A1 | 2/2009 | Cheng |
| 2010/0076690 | A1 * | 3/2010 | Reja et al. ....................... 702/19 |

FOREIGN PATENT DOCUMENTS

| WO | 03/078625 A2 | 9/2003 |
| WO | 2005/071113 A1 | 8/2005 |
| WO | 2005/113819 A2 | 12/2005 |
| WO | WO 2007/035808 | 3/2007 |

OTHER PUBLICATIONS

Supplementary European Search Report mailed Jul. 20, 2012, EP10746925, 10 pages.
Paterlini, S., et al., "High performance clustering with differential evolution," Evolutionary Computation, Jun. 2004, IEEE, vol. 2, pp. 2004-2011.
International Search Report and Written Opinion dated Apr. 26, 2010 in related International Application No. PCT/US2010/025614, filed Feb. 26, 2010.
Nellaker et al., "Mixture models for analysis of melting temperature data," 2008, BMC Bioinformatics, 9; 370.

* cited by examiner

*Primary Examiner* — Mary Zeman
(74) *Attorney, Agent, or Firm* — Kilpatrick Townsend & Stockton LLP

(57) ABSTRACT

Systems, methods and apparatus for an automated analysis of a collection of melt curves is provided. The analysis can identify certain characteristics of double stranded nucleotide sequences (e.g. DNA or other nucleotide sequences) which were melted. For example, a variation (e.g. a mutation) in the sequences (also called amplicons) may be determined from the analysis. The amplicons may be amplified via any amplification mechanism, such as PCR or Ligase chain reaction (LCR). The automated analysis can include identifying a melt region, normalizing a melt curve, and clustering melt curves.

24 Claims, 13 Drawing Sheets

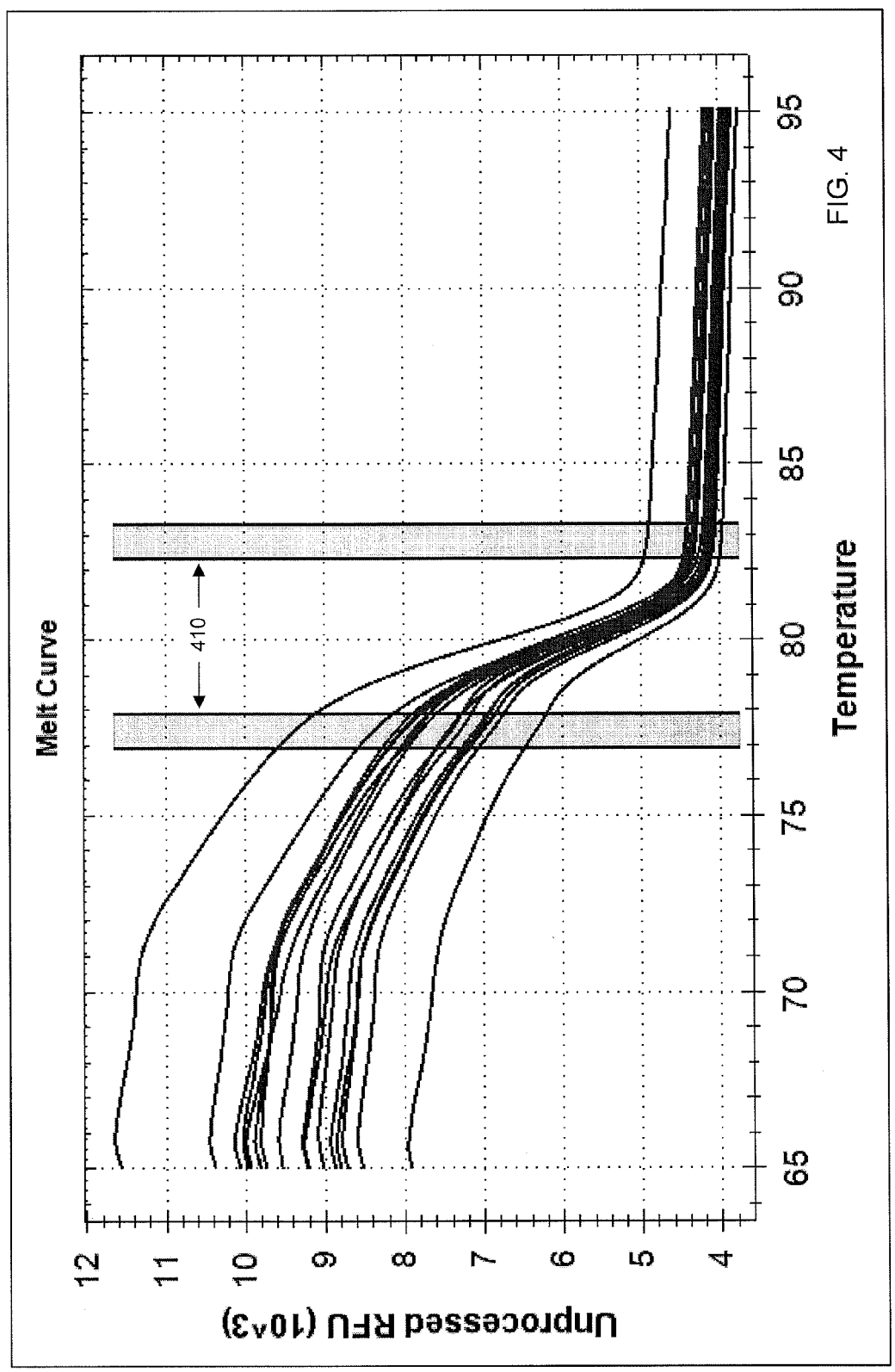

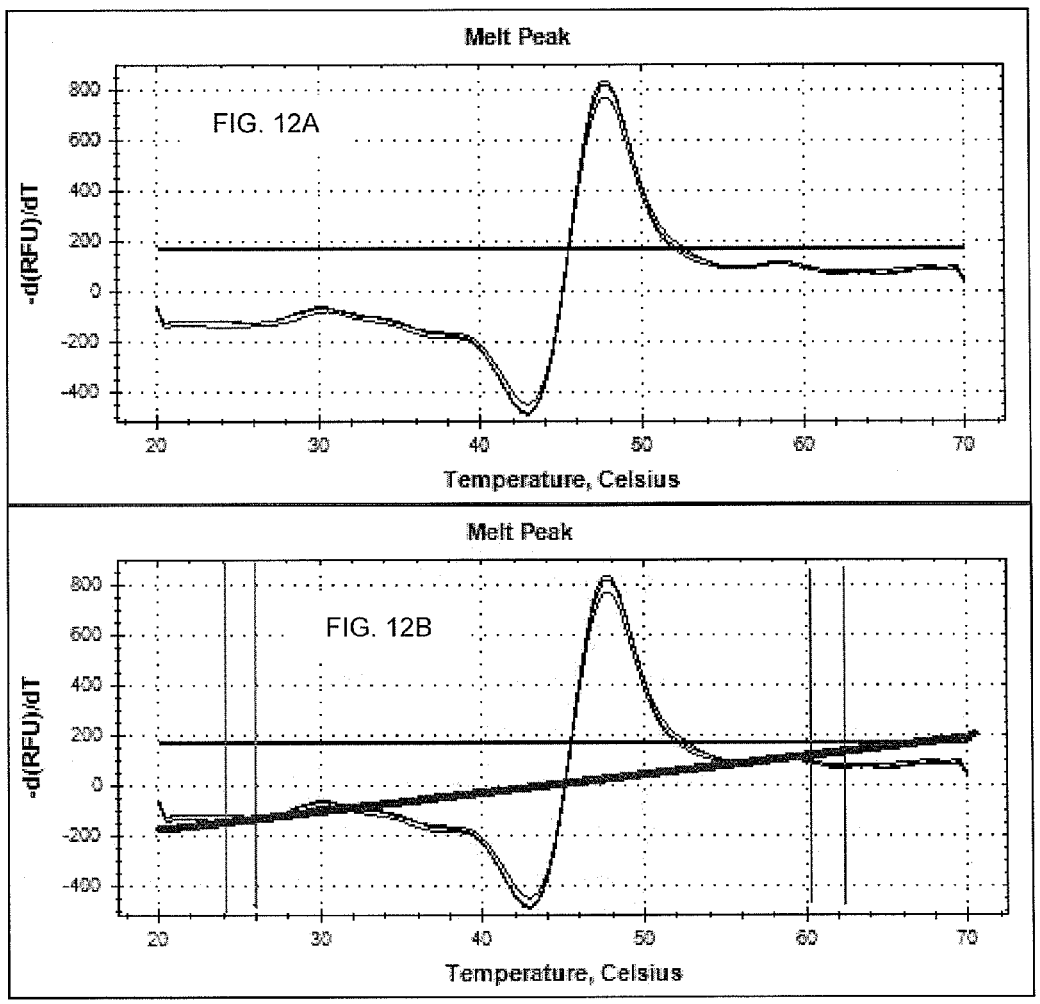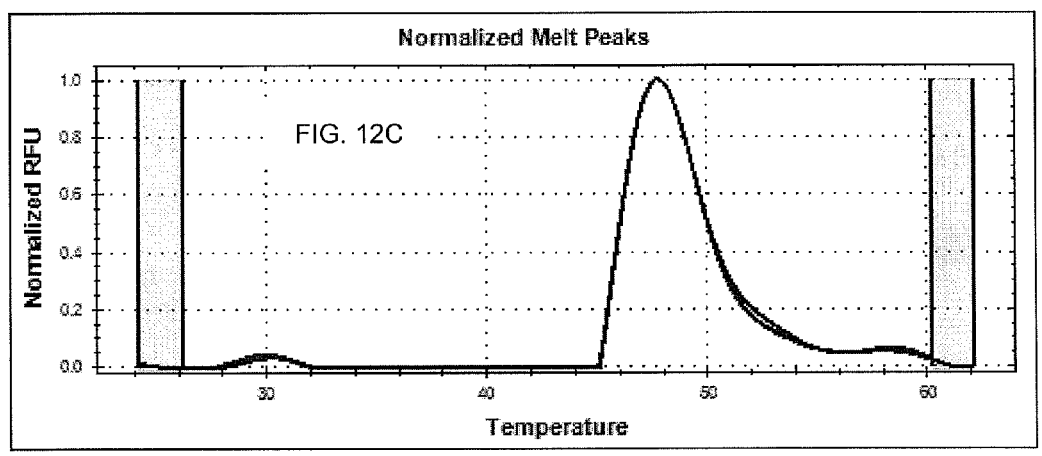

SNP DETECTION BY MELT CURVE CLUSTERING

CROSS-REFERENCES TO RELATED APPLICATIONS

This non-provisional patent application claims priority to U.S. Provisional Patent Application No. 61/156,034, entitled SNP Detection by Melt Curve Clustering, filed on Feb. 27, 2009. This provisional application is incorporated by reference herein in its entirety for all purposes.

BACKGROUND

The present invention generally relates to identifying sequence variations in genes, such as single nucleotide polymorphisms (SNP), and more specifically to using melt curves from polymerase chain reactions (PCR) apparatus to identify the sequence variations.

Real-time PCR is used to detect and quantify target nucleotide sequences. In PCR, one or more reaction wells contain a DNA template that contains the DNA region (target) to be amplified. The temperature of the reaction well is increased so that the DNA dissociates into two single strands. The temperature is then lowered so that primers that are complementary to the area flanking the target sequence then bind. The temperature is then increased slightly to dissociate the single strand and primer bond. The DNA polymerase can then synthesize a new DNA to provide for amplification of the DNA.

The exponential amplification of a sequence is monitored in real time, e.g., by fluorescence. Commonly, a fluorescent dye is used, which only reports the presence of double-stranded DNA. Typically, the dyes do not distinguish sequences and can thus report the amplification of undesired targets. These undesired sequences can be detected during a dissociation step. During dissociation, the doublestranded PCR products melt into single strands, so fluorescence is diminished. Often a melting process is performed after amplification has been fully achieved.

A melt curve can be produced by plotting the loss of fluorescence against a gradual increase in temperature. The detection of different melt curves implies the presence of different sequences. This technique has been used for the detection of single-nucleotide polymorphisms, allelic discrimination, and strain typing of microorganisms.

However, the determination of differences among different melt curves is difficult and may not be repeatable. Therefore, improved methods and systems for detecting sequence variation using melt curves is desirable to provide greater accuracy, reliability, and consistency of the results.

SUMMARY

Embodiments of the invention can provide systems, methods, and apparatus for an automated analysis of a collection of melt curves. The analysis can identify certain characteristics of double stranded nucleotide sequences (e.g. DNA or other nucleotide sequences) which were melted. For example, a variation (e.g. a mutation) in the sequences (also called amplicons) may be determined from the analysis. The amplicons may be amplified via any amplification mechanism, such as PCR or Ligase chain reaction (LCR). Various embodiments can provide methods for identifying a melt region, for normalizing a melt curve, and for clustering melt curves, which may be done after normalization.

According to some embodiments, methods of identifying a sequence variation between nucleotide sequences are provided. A plurality of sets of data points are received, each set corresponding to a different sample that contains copies of a double stranded molecule of two nucleotide sequences. Each data point of a set includes a signal value and a temperature value for the sample where the temperature increases for each successive data point. Each set defines a melt curve.

In one embodiment, a processor determines a melt region for the melt curves. For each melt curve, a second derivative is taken, and start and end temperatures where a function of the second derivative crosses a boundary threshold value are identified. Based on the respective start temperatures of the melt curves, a melt region start is identified. Based on the respective end temperatures of the melt curves, a melt region end is identified. Each melt curve is assigned to a respective cluster. The melt curves assigned to a same cluster have one or more similar properties in the melt region relative to melt curves in other clusters. At least a portion of the nucleotide sequences corresponding to at least one cluster are identified as having a sequence variation relative to the nucleotide sequences of another cluster.

In another embodiment, a melt region having a melt region start and a melt region end is determined. A processor performing a first normalization of each melt curve by: modifying the data points of the melt curve so that data points within an end region have an average value of a first number, and modifying the data points of the melt curve such that the data points in a start region have an average value of a second number. The end region is a temperature range starting at the melt region end, and the start region is a temperature range ending at the melt region start. For each melt curve, a threshold temperature at which the melt curve crosses a threshold is identified. An average threshold temperature from the respective threshold temperatures is calculated. Each melt curve is shifted so that the melt curve crosses the threshold at the average threshold temperature. A second normalization of each melt curve includes modifying the data points of the melt curve having a lower temperature than the average threshold temperature such that the data points in the start region have an average value of a third number. Each melt curve is assigned to a respective cluster. The melt curves assigned to a same cluster have one or more similar properties in the melt region relative to melt curves in other clusters. At least a portion of the nucleotide sequences corresponding to at least one cluster are identified as having a sequence variation relative to the nucleotide sequences of another cluster.

In another embodiment, a melt region having a melt region start and a melt region end is determined. Each melt curve is assigned to a respective cluster. The melt curves are assigned to a same cluster have one or more similar shape properties in the melt region relative to melt curves in other clusters. A processor selects a cluster of melt curves, and determines a melting temperature of each melt curve of the selected cluster. The processor groups the melt curves of the selected cluster into a plurality sub-clusters based on the respective melting temperatures. At least a portion of the nucleotide sequences corresponding to at least one sub cluster are identified as having a sequence variation relative to the nucleotide sequences of another sub-cluster.

In another embodiment, a melt region having a melt region start and a melt region end is determined. At least one processor assigns each melt curve to a respective cluster by analyzing shapes of the melt curves. The melt curves assigned to a same cluster have one or more similar shape properties in the melt region relative to melt curves in other clusters. Analyzing shapes includes: for each melt curve, calculating N average values, each value the average of one of a plurality of continuous segments of the melt curve; defining the set of N average values as a point in N-dimensional space; fitting the N-dimensional points to K N-dimensional functions; identifying each N-dimensional point with one of the K N-dimensional functions; and grouping the melt curves associated with a same N-dimensional function into a same cluster. At least a portion of the nucleotide sequences corresponding to at least one cluster are identified as having a sequence variation relative to the nucleotide sequences of another cluster.

In another embodiment, a melt region having a melt region start and a melt region end is determined. At least one processor takes a negative first derivative of each melt curve to determine respective melt peak curves. The at least one processor assigns each melt curve to a respective cluster. The melt curves assigned to a same cluster have one or more similar properties for the melt peak curves in the melt region relative to melt curves in other clusters. At least a portion of the nucleotide sequences corresponding to at least one cluster are identified as having a sequence variation relative to the nucleotide sequences of another cluster.

Embodiments are also directed to computer readable medium and systems that implement methods described herein.

A better understanding of the nature and advantages of the present invention may be gained with reference to the following detailed description and the accompanying drawings.

BRIEF DESCRIPTION OF THE DRAWINGS

FIG. 4 shows a plot 400 illustrating a melt region 410 for a set of melt curves according to an embodiment of the present invention.

FIG. 12A shows melt peak curves according to an embodiment of the present invention. FIG. 12B shows a plot of the baseline of the melt peak curves in FIG. 12A. FIG. 12C shows the resulting data from subtracting out the baseline shown in FIG. 12B.

DETAILED DESCRIPTION

Figure 1:
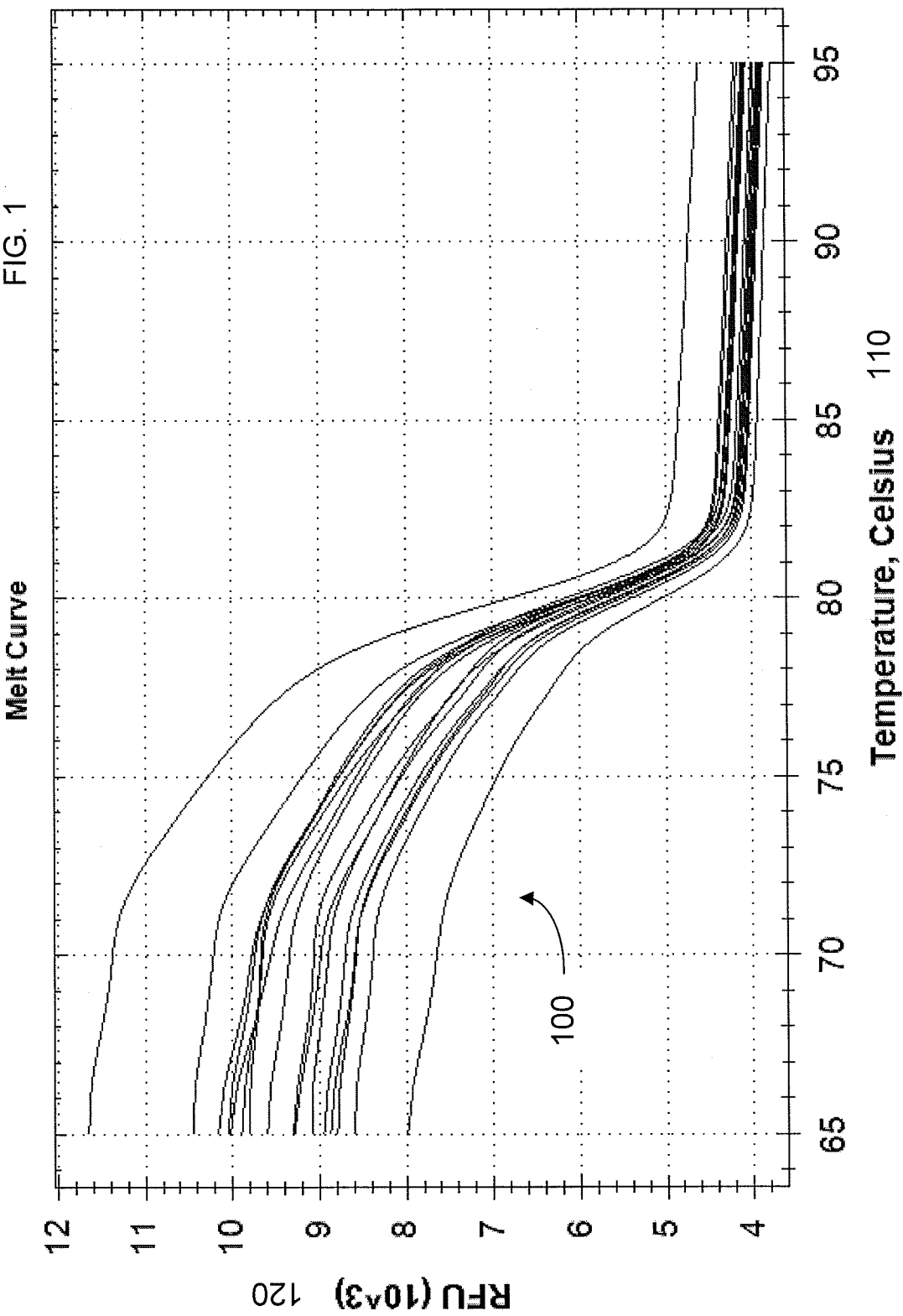
FIG. 1 shows a set of melt curves 100, each corresponding to a different double stranded nucleotide sequence according to an embodiment of the present invention.

FIG. 1 shows a set of melt curves 100, each corresponding to a different double stranded nucleotide sequence according to an embodiment of the present invention. The melt curves may be generated in any fashion known to one skilled in the art. The X axis 110 is temperature in Celsius. The temperature decreases over time, and thus the temperature is also correlated to time. In one embodiment, the correlation may be linear, although other relationships may occur in other embodiments. The Y axis 120 provides a value of a signal obtained from the amplicons, e.g. a fluorescent signal. The units shown are relative fluorescence units (RFU).

The higher the RFU is the greater the amount of double stranded DNA (dsDNA). The less the value for the RFU is the lower the amount of double stranded amplicons. The temperature at which a sample of dsDNA melts (melting temperature) can be determined as a point where the RFU has dropped below a certain level. At this point, the dsDNA can be considered to have melted.

Each melt curve has a certain shape and/or melting temperature, depending on certain characteristics of its amplicon. Characteristics which give rise to differences in that melt curve shape and melting temperature include the sequence of the amplicon. In one aspect, the sequence can have the greatest effect on the melting temperature.

Whether the amplicon contains a heterozygous mutation also can affect the melt curve shape and melting temperature. In one aspect, the existence of a heterozygous mutation can have the greatest effect on the shape of the melt curve. Amplicons which contain heterozygous single nucleotide polymorphisms (SNPs) give rise to a mixture of dsDNA after amplification. Roughly half of the resulting dsDNA have a mismatched base pair at the SNP location, with one strand coming from the parent that has the SNP, and the other not. The dsDNA that contains the base pair mismatch is less stable and will melt at a slightly lower temperature. This instability causes a characteristic early dip in the melt curve. The degree of methylation within the amplicon can also impact the shape and melting temperature.

I. General Method

Figure 2:
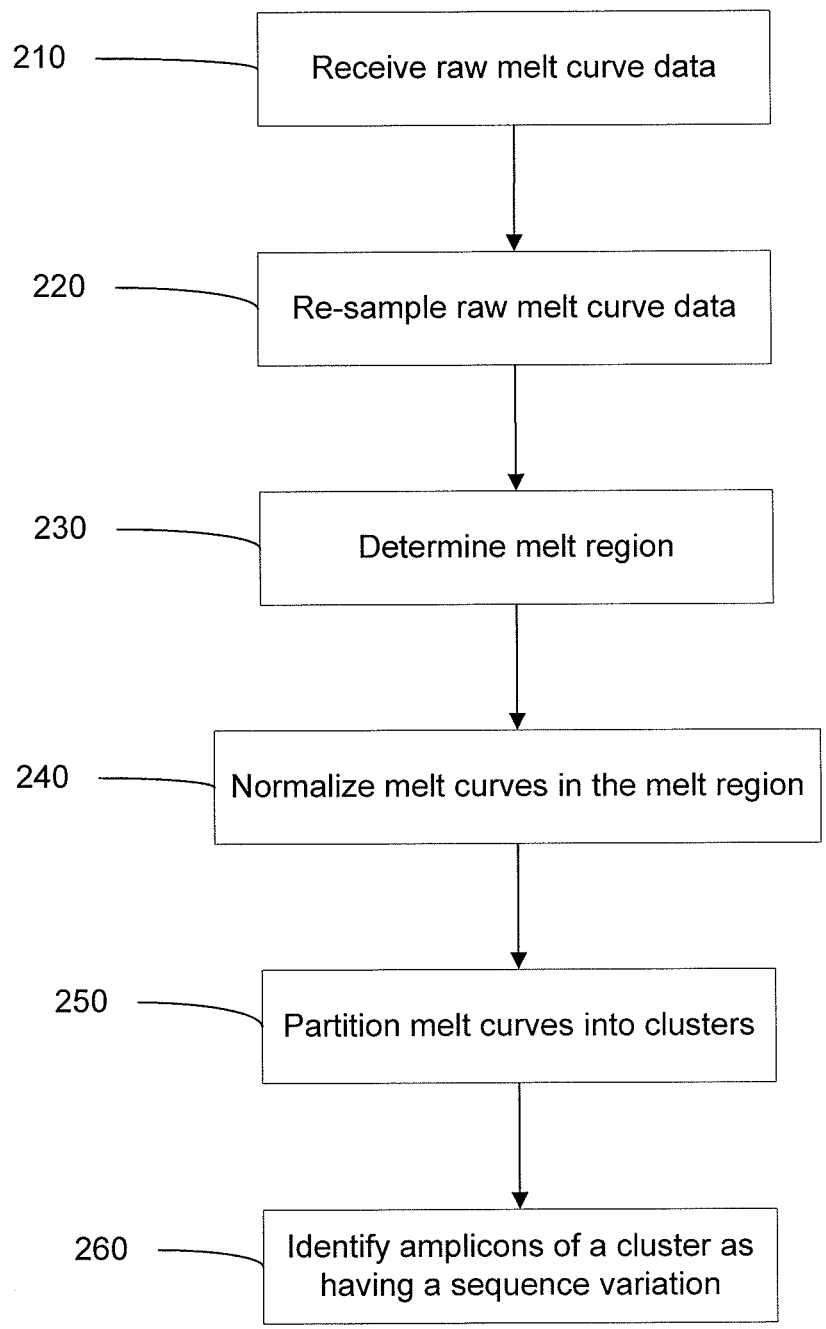
FIG. 2 is a flowchart illustrating a method for analyzing melt curves of amplicons to determine a sequence variation of the amplicons according to an embodiment of the present invention.

FIG. 2 is a flowchart illustrating a method 200 for analyzing melt curves of amplicons to determine a sequence variation of the amplicons according to an embodiment of the present invention. Method 200 may be implemented by a computer system having at least one processor and any number of storage units for storing data and/or program code for controlling the at least one processor.

In step 210, the raw melt curve data is received, for example, at an input of a computer system that is part of or networked with the amplification apparatus (e.g. a PCR machine). In one embodiment, the raw melt curves are a plurality of sets of data points. In one aspect, each set can define a melt curve and can correspond to a different melt curve. In another aspect, each melt curve may be from a different sample (e.g. a reaction well) that contains copies of a double stranded molecule (e.g. a gene) of two nucleotide sequences. Each data point of a set can include a signal value and a temperature value for the sample where the temperature increases for each successive data point.

In step 220, the raw melt curve data is re-sampled. The re-sampling involves any type of curve fitting, interpolation, or regression. For example, the data may be interpolated using cubic splines. The resulting interpolation may be sampled at any frequency to give new data points, e.g., such that there is one data point per tenth of a degree Celsius. In one aspect, the use of a spline (or other method) allows fewer data points to be measured by the PCR machine. In other embodiments, the raw melt curve data may be used without re-sampling.

In step 230, the melt region is determined. The melt region may be considered as the region which begins just prior to the start of the dsDNA disassociation, and ends just after the dsDNA is fully disassociated. Method 300 described below provides one example of a way of finding the melt region.

In step 240, each melt curve is normalized in the melt region. In one embodiment, the normalization is performed to set values near the start and end of the melt region. This normalization may be viewed as a single normalization process as is described later. In another embodiment, the normalization fixes a third point within the normalization region. In another embodiment, the normalization may convert the melt curve to a new function and then normalize the new function. For example, the melt curves could be converted into the negative first derivative of the melt curve, and then the negative first derivatives normalized.

In step 250, the melt curves are partitioned into clusters. In one aspect, each melt curve is assigned to one cluster. The determination of the assignment can be made in various ways, e.g., as described below. A determination of how many clusters will be used in a clustering may be performed as described in FIG. 10

In step 260, at least a portion of the nucleotide sequences corresponding to at least one cluster as having a sequence variation (e.g., a gene mutation). In one embodiment, each melt curve is from a different well of a PCR plate. Also, each well may be of the same gene, but from a different person. The wells that show a sequence variation can be determined as exhibiting a mutation in the gene.

The variation determination may be made relative to the nucleotide sequences of another cluster (e.g. the cluster that contains the most melt curves). For example, the melt curves of the gene that is the wild type (most common) can then be differentiated from the melting curves where the gene has a mutation. If there is no wild type then the sequences can be compared to a reference melt curve to determine whether a sequence variation is a mutation.

Once a gene is identified as having a mutation then further analysis (such as the more costly sequencing) may be performed to determine the type of mutation. Note that not all of the sequences of the cluster determined as having the variation necessarily have the variation. For example, in a heterozygous SNP, only one of the sequences of the dsDNA has a mutation. In one aspect, the primers used would encompass the site of the mutation.

II. Identification of Melt Region

Figure 3:
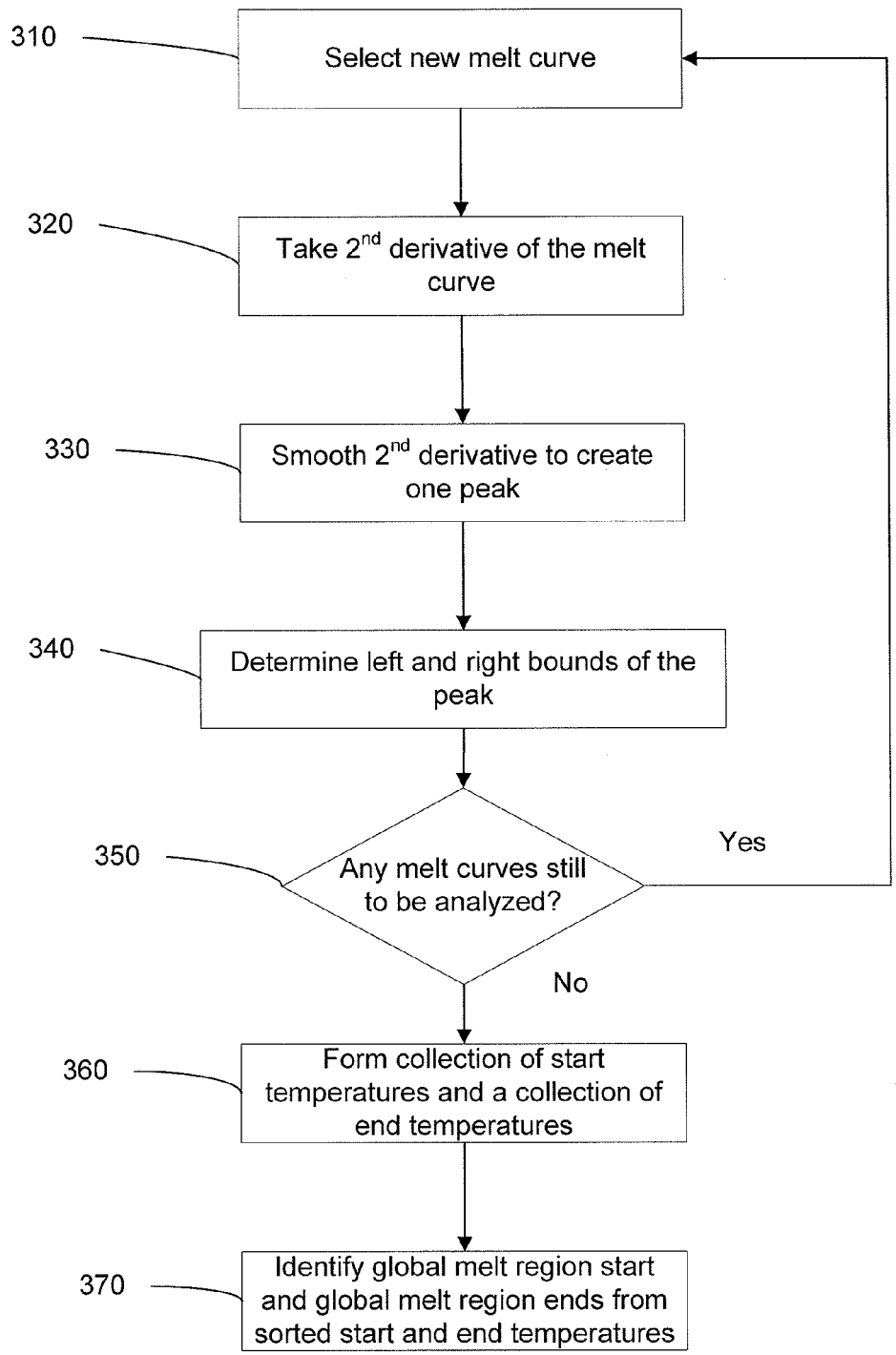
FIG. 3 is a flowchart illustrating a method for analyzing a set of melt curves to determine a global melt region according to an embodiment of the present invention.

FIG. 3 is a flowchart illustrating a method 300 for analyzing a set of melt curves to determine a global melt region according to an embodiment of the present invention. Method 300 may be used to implement step 230 of method 200. For each melt curve, a melt region for that melt curve is determined, and then a global melt region is determined from the individual melt regions.

In step 310, a new melt curve that has not been analyzed is selected. In one embodiment, all melt curves received are analyzed. In another embodiment, only certain melt curves of all the melt curves received are selected for analyzing.

In step 320, the second derivative of the selected melt curve is taken. In one embodiment, the absolute value of the second derivative is used in the analysis. In one aspect, the value of the second derivative is typically near-zero except in areas of interest, e.g., just before and just after the melt region. In another aspect, the second derivative can have two peaks, with one peak at melt region start and one peak at the melt region end.

In step 330, the second derivative curve is smoothed (e.g. with a smooth-width of 2 degrees Celsius), which merges the two peaks into one peak. A result can be one broad peak across the melt region while leaving the rest of the data near-zero. In one embodiment, the smoothing function takes an average of the data points within a window (e.g. 2°) around a specific data point, and then uses that average as the new value for that data point. A smoothing can reduce the effect of noise.

In step 340, left and right bounds of the one merged peak are determined. In some embodiments, the left and right bound are points where the peak crosses a threshold value. The threshold value may be a fixed number or a value relative to a characteristic of the peak (such as the maximum value of the peak). Thus, in one embodiment, the left and right bounds of the peak are identified as where the peak crosses a boundary threshold of peak max*0.35 on its left and right. Those boundary threshold crossings can be used as the melt curve's melt region bounds.

An advantage of such methods is that the edges of the melt curve are found, and not just a central point of the melt curve, which may be found with a first derivative. With a melt region defined, the melt curves' shapes can be compared more accurately and consistently. Also, the second derivative can be less susceptible to differences in the regions outside of the desired melt region, as the second derivative tends to be small in these outside regions.

In step 350, it is determined whether any more melt curves need to be analyzed. If more curves are to be analyzed, then the process returns to step 310 to select a new melt curve.

In step 360, a collection of the start temperatures for each melt curve are determined from the left bounds, and a collection of the end temperatures for each melt curve are determined from the right bounds, from step 340. In one embodiment, those two collections are sorted in ascending or descending order.

In step 370, a global melt region start and a global melt region ends are determined from the respective start and end temperatures of the curves. In some embodiments, a respective start temperature is identified that is greater than a predetermined number of other start temperatures as the global melt region start, and a respective end temperature is identified that is less than a predetermined number of other end temperatures as the melt region end.

In one embodiment, the 15-35% (e.g. the $25^{th}$) percentile value (i.e. greater than 25% of other starts) from the sorted start temperatures is taken as the global melt region start, and the 65-85% (e.g. the $75^{th}$) percentile value (i.e. less than 75% of other ends) from the sorted end temperatures is taken as the global melt region end. In this manner, outlying data points do not have a disproportionate effect, while still analyzing data points that a substantial portion of the melt curves deemed significant (i.e. higher than the boundary threshold). In another embodiment, an average, median, or other function of the respective start and end temperatures of the curves may be used.

FIG. 4 shows a plot 400 illustrating a melt region 410 for a set of melt curves according to an embodiment of the present invention. As one can see from this embodiment, the melt curves can begin to decrease before the start of the melt region. The melt region advantageously allows the analysis of the shape and melting temperatures of the curves to be performed over a reproducible region that is of particular and consistent significance to the melt curves. The determination of the clusters can be more accurate when the analysis is confined to the melt region.

III. Two-Step Normalization

The melt region may then be used to normalize the melt curves, e.g., to provide greater consistency and accuracy in the analysis of the shape and temperatures. In one embodiment, each melt curve is normalized such that the melt curve has a first value (e.g. 0) at the melt region end and a second value (e.g. 1) at the melt region start.

Figure 5A:
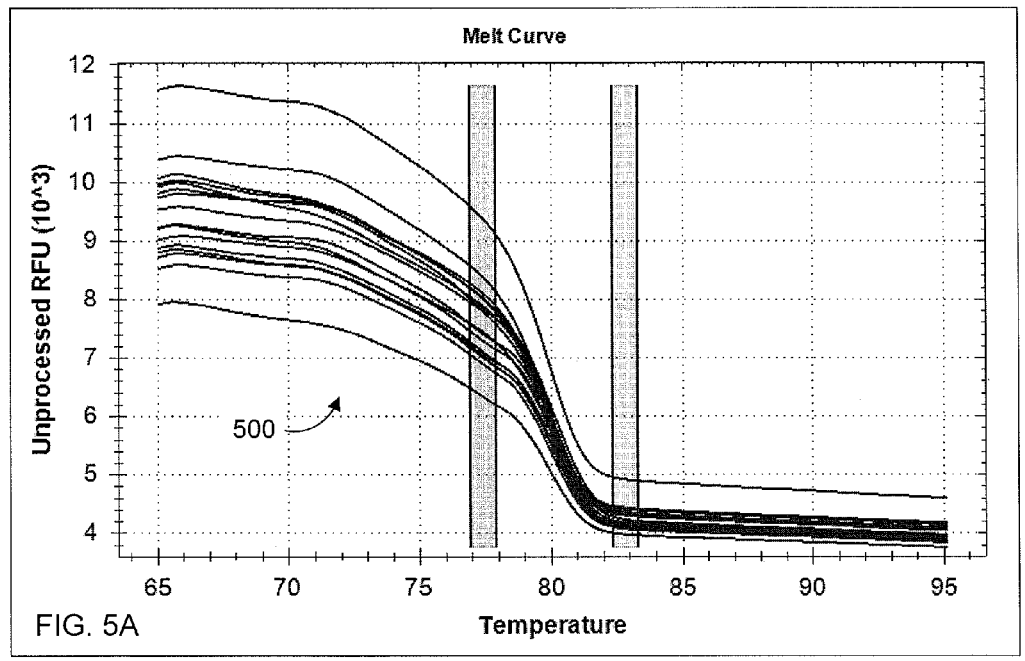
FIG. 5A shows an unnormalized set of melt curves 500 according to an embodiment of the present invention.
Figure 5B:
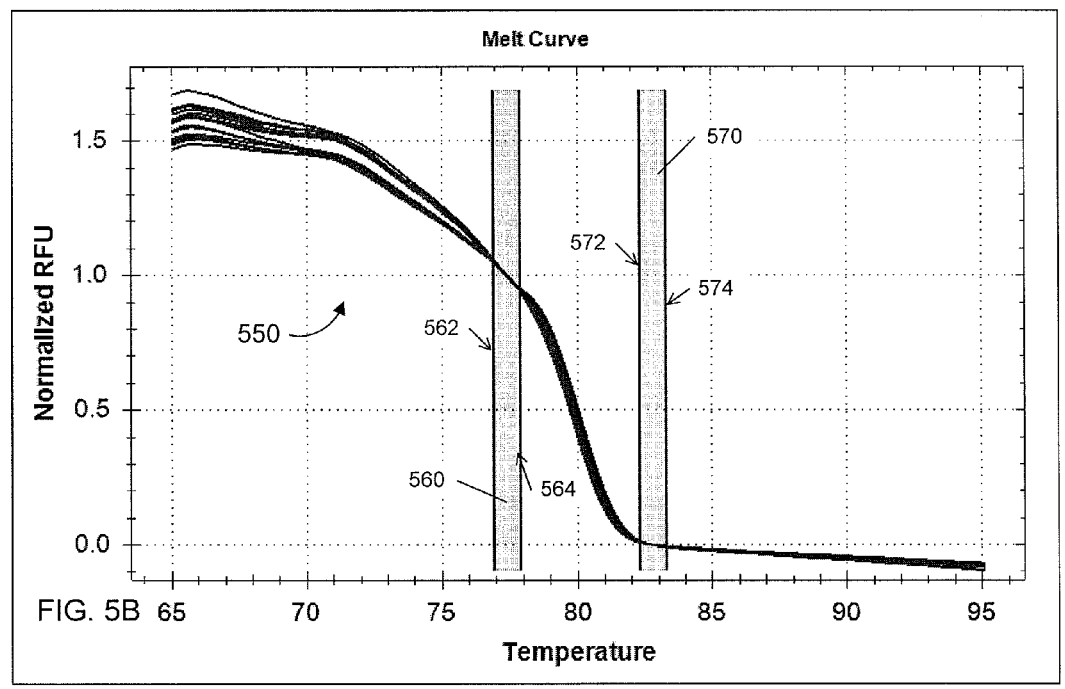
FIG. 5B shows a normalized set of melt curves 550 according to an embodiment of the present invention.

FIG. 5A shows an unnormalized set of melt curves 500 according to an embodiment of the present invention. FIG. 5B shows a normalized set of melt curves 550 according to an embodiment of the present invention. As shown, the normalized melt curves have a value of "1" in the left vertical bar 560 and a value of "0" in the right vertical bar 570.

The left vertical bar 560 is the start region. The start region ends 564 at the melt region start and begins 562 at a specified (e.g. predetermined) temperature range prior to the start. The right vertical bar 570 is the end region. The end region starts 572 at the melt region end and ends 574 after a specified (e.g. predetermine) temperature range from the melt region end. For example, the range may be 0.5° C.-1.0° C.

Figure 6:
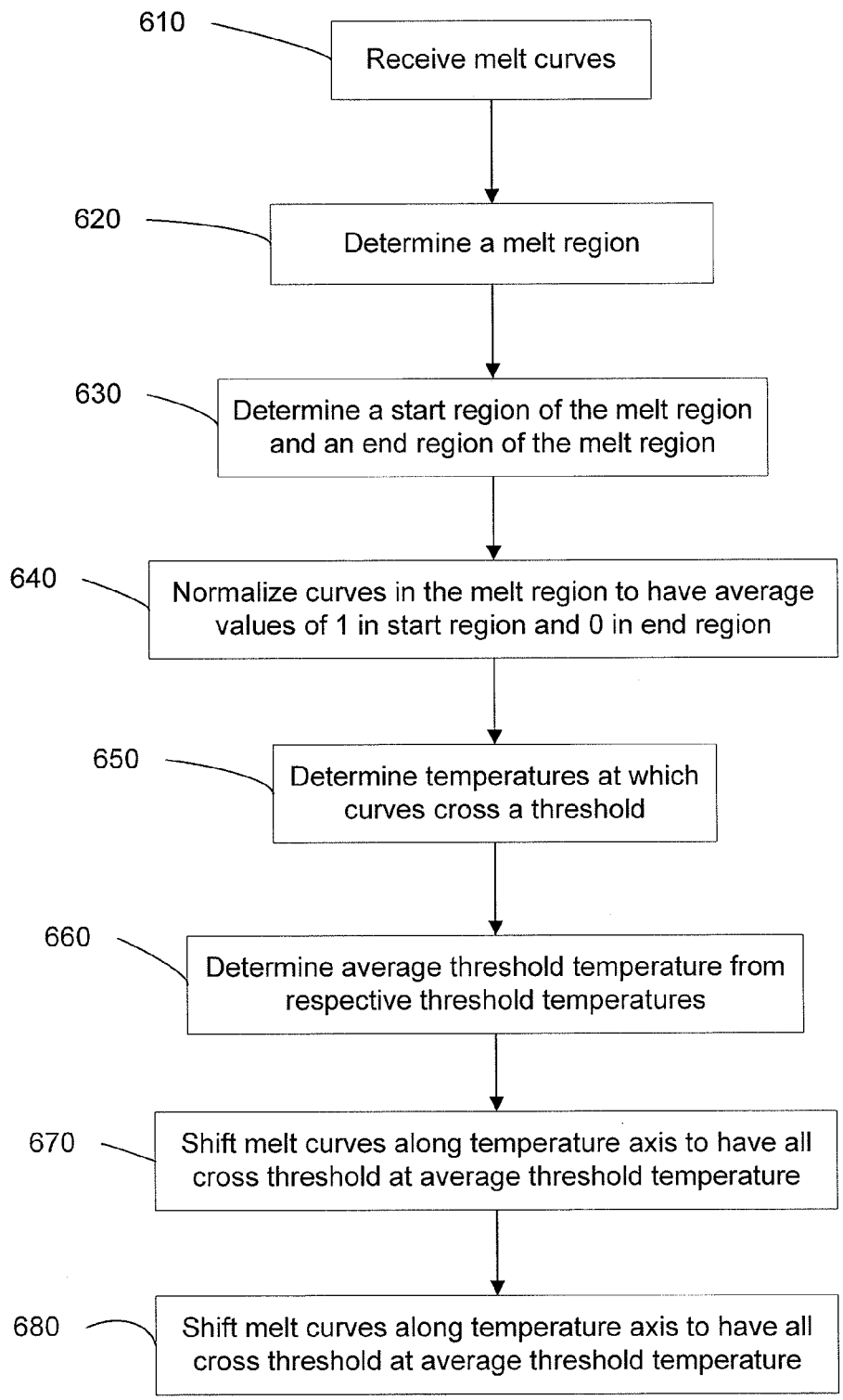
FIG. 6 is a flowchart illustrating a method 600 of normalizing melt curves within a melt region according to an embodiment of the present invention.

FIG. 6 is a flowchart illustrating a method 600 of normalizing melt curves within a melt region according to an embodiment of the present invention. For completeness, method 600 starts from receiving the melt curve data.

In step 610, melt curves are received. The received melt curves may be the raw melt data or re-sampled data. In step 620, a melt region having a melt region start and a melt region end is determined. The melt region may be determined by method 300 or any other method. For example, a temperature window centered around a peak of a first derivative of one or more of the melt curves may be used.

In step 630, an end region of the melt region is determined. In one aspect, the end region is of a temperature range (which may be predetermined, e.g. 0.5° C.) starting at the melt region end. A start region of the melt region may also determined. In another aspect, the start region is of a temperature range (which may be predetermined) ending at the melt region start.

In step 640, a first normalization of each curve is performed. In one embodiment, for each curve, the normalization is performed by offsetting the data points of that curve so that the data points within the end region have an average value of a first value (e.g. 0). Then, the curve is multiplied by a number such that the data points in the start region have an average value of a second value (e.g. 1).

In step 650, for each curve normalized once, a threshold temperature is identified at which the curve crosses a melting threshold. In one embodiment, the melting threshold is empirically derived. Common values are between 0.5 and 0.2. This value may depend on the quality of the melt curves. In various embodiments, data with low noise can have a lower melting threshold, and data with higher noise can have a higher melting threshold.

In step 660, an average threshold temperature is calculated from the respective threshold temperatures. In one embodiment, the average is a simple average of the sum of the respective threshold temperatures divided by the number of respective threshold temperatures. In another embodiment, the average can be weighted or functions of the respective threshold temperatures may be taken before the average is performed.

In step 670, the melt curves are shifted along the temperature axis so that each melt curve crosses the threshold at the average threshold temperature. But after the shift, the values in the end and start regions are no longer the desired first and second values.

In step 680, a second normalization is performed. The data points of the curve having a higher temperature than the average threshold temperature can be modified such that the data points of the curve have a value of the threshold at the average threshold temperature and an average value of a third number (e.g. 0) in the end region. The data points of the curve having a lower temperature than the average threshold temperature can be modified such that the data points in the start region have an average value of a fourth number (e.g. 1).

This normalization advantageously allows the analysis of the shape and melting temperatures of the curves to be performed in a uniform manner with greater consistency, regardless of noise in signals. The determination of the clusters can be more accurate when the analysis is performed on melt curves that are compared after such a normalization.

Figure 7A:
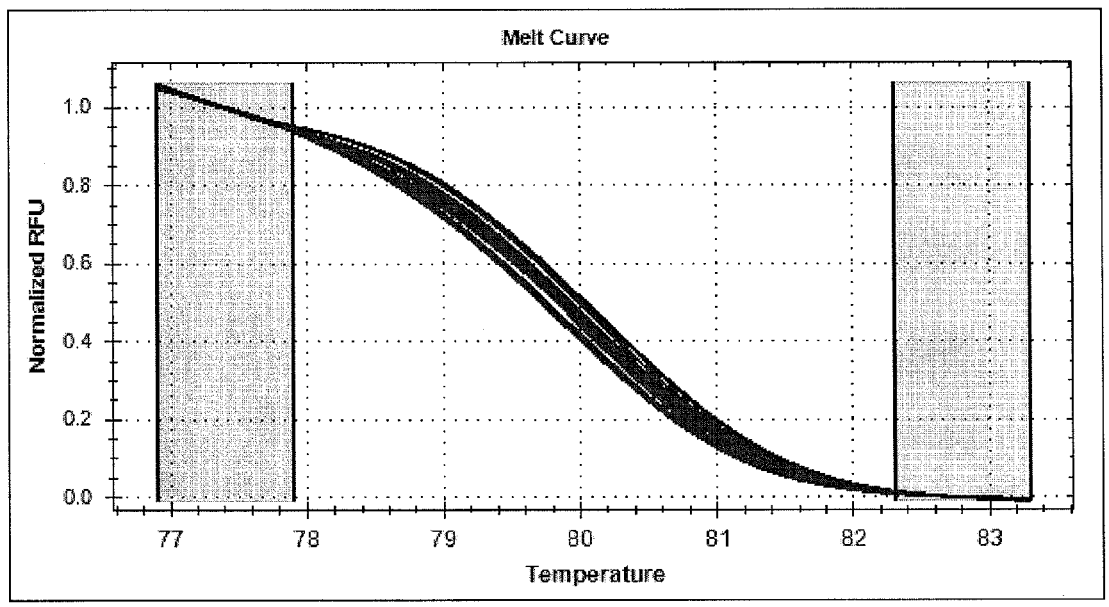
FIG. 7A shows a set of melt curves that have undergone only a first normalization according to an embodiment of the present invention.

FIG. 7A shows a set of melt curves that have undergone only a first normalization according to an embodiment of the present invention. As one can see, the melt curves span a range of values throughout the melt region. Such dispersion can cause difficulties and irregularities in a shape analysis.

Figure 7B:
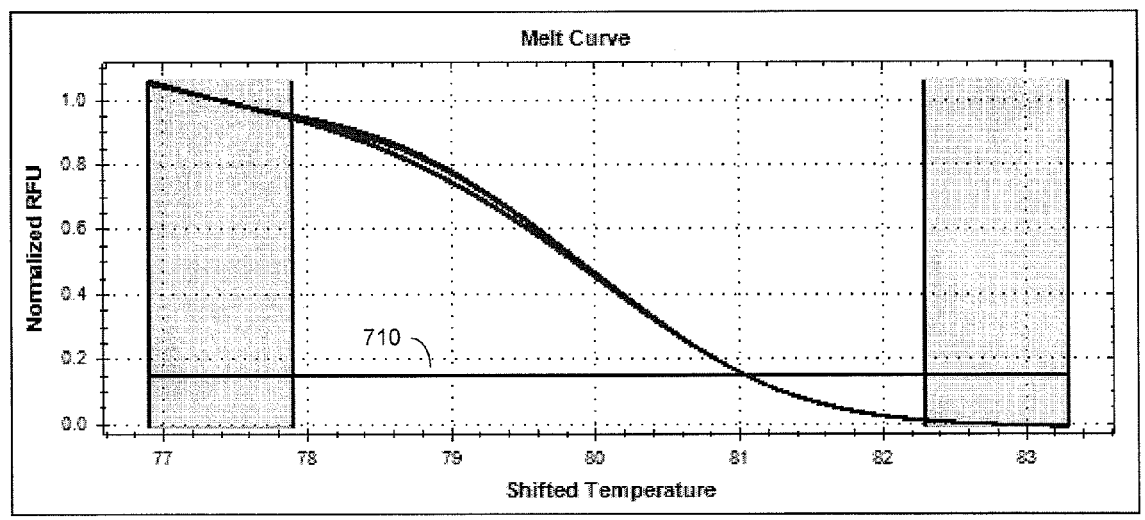
FIG. 7B shows a set of melt curves that have undergone a second normalization according to an embodiment of the present invention.

FIG. 7B shows a set of melt curves that have undergone a second normalization according to an embodiment of the present invention. As one can see the dispersion of the melt curves among different values in the melt region has been lowered. Each of the melt curves crosses the threshold 710 at the same temperature, the average threshold temperature (about 81°), as determined in step 660. The second normalization is performed separately for points above and below the average threshold temperature such that each melt curve still crosses the threshold at the average threshold temperature.

IV. Two-Tiered Clustering

Different types of sequence variations can result in different behavior. Embodiments can use a two step process to more efficiently and accurately identify different types of sequence variations.

Figure 8:
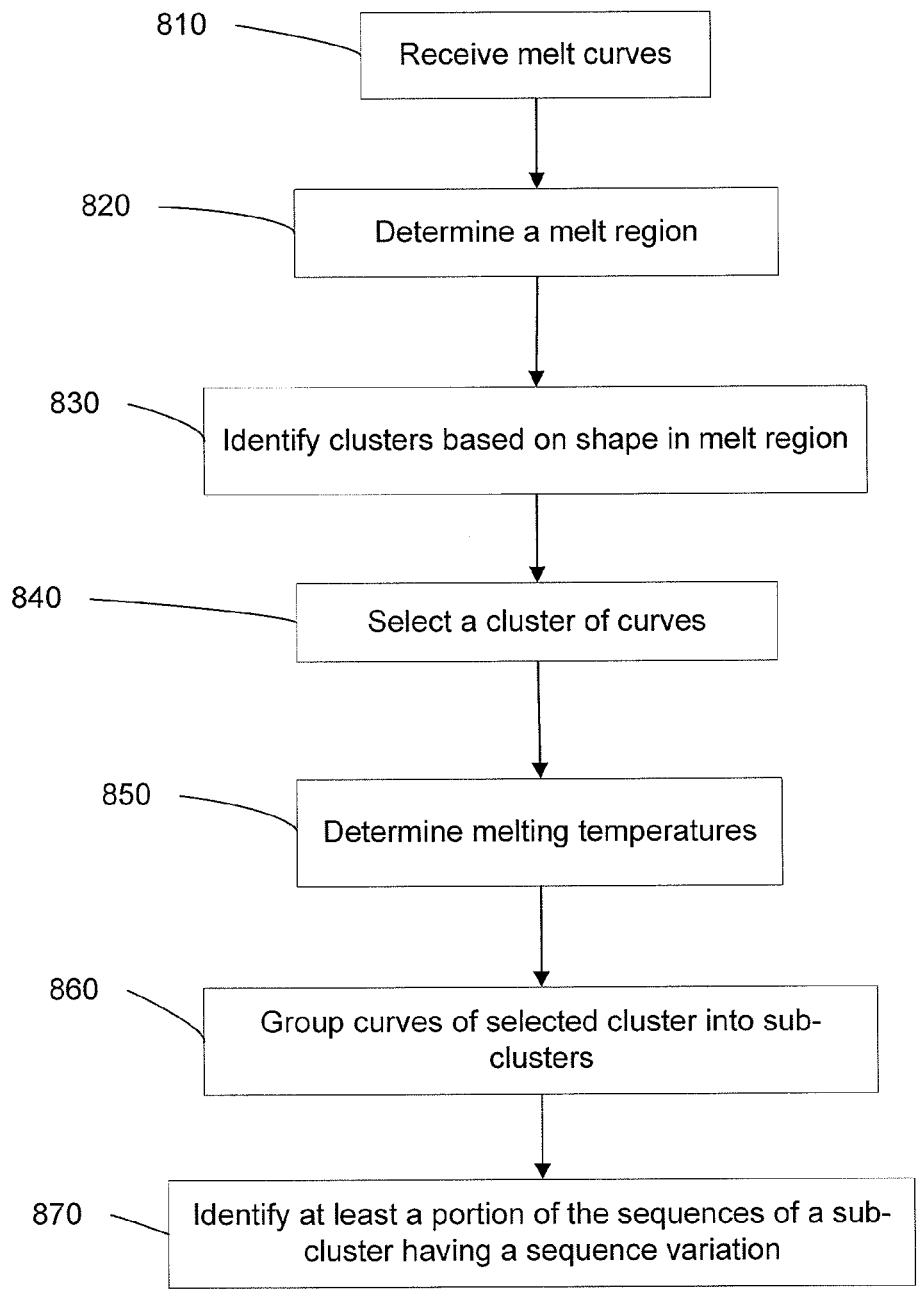
FIG. 8 is a flowchart illustrating a method 800 for identifying sequence variation within a sub-cluster according to an embodiment of the present invention.

FIG. 8 is a flowchart illustrating a method 800 for identifying sequence variation within a sub-cluster according to an embodiment of the present invention. The set of melt curves can be partitioned into clusters and then into sub-clusters. In one embodiment, shape clusters are first found, then melting temperature sub-clusters are found within each shape cluster. In one aspect, shape clustering can differentiate the melt curves that correspond to heterozygous mutations from those which do not, while melting temperature clustering can differentiate the melt curves which have homozygous mutations from those which do not.

In step 810, the melt curves are received, e.g., as described herein. In step 820, a melt region having a melt region start and a melt region end is determined, e.g., as described herein.

In step 830, different clusters of curves are identified as having different melt profiles by analyzing shapes of the curves in the melt region. For example, a heterozygous SNP will have a different shape than the wild type. Typically, the heterozygous SNP will decrease faster at first than the wild type, and then have an elbow where the descent of the melt curve flattens out a bit. This is a result of there being two different sequences in the well, since only one of the chromosomes has a sequence variation. In one aspect, there will be four different dsDNA amplicons in the well in this case: homoduplex wild type (from parent 1), homoduplex SNP (from parent 2), and two heteroduplex products (one comprised of strand 1 from parent 1 and strand 2 from parent 2, and one comprised of strand 2 from parent 1 and strand 1 from parent 2.)

In step 840, a cluster is selected. In one embodiment, the selected cluster is the cluster that corresponds to the cluster that the wild type is in. Thus, in one embodiment, the selected cluster is the cluster with the largest number of melt curves. In another embodiment, each of the shape clusters are selected for further respective analysis per the steps below. Sequences not in the wild type cluster may be identified as having a heterozygous SNP.

In step 850, a melting temperature of each curve of the selected cluster is determined. The melting temperature may be derived by a standard means of discovering the peak location within the negative first derivative. In one embodiment, the melt curve data used for this is the non-temperature shifted, RFU normalized data. In another embodiment, the melting temperature is a value at which the melt curves cross a threshold value.

In step 860, the curves of the selected cluster are grouped into a plurality sub-clusters based on the respective melting temperatures. In one embodiment, a same computational method for grouping the curves by shape is used to perform the grouping by melting temperature. In another embodiment, the melting temperature is determined from the unnormalized melt curves by any method, such as a peak of a first derivative or by a temperature where the melt curve crosses a threshold value.

In step 870, at least a portion of the sequences of a sub-cluster are identified as having a sequence variation. For example, a gene of a sub-cluster may be identified as having a mutation, such as a homozygous SNP. In this manner, heterozygous SNPs may be determined first by analyzing the shape. Then, homozygous SNPs can be more easily identified by analyzing only within a cluster that has the same shape.

V. Clustering Shapes by Fitting to K N-Dimensional Functions

Figure 9:
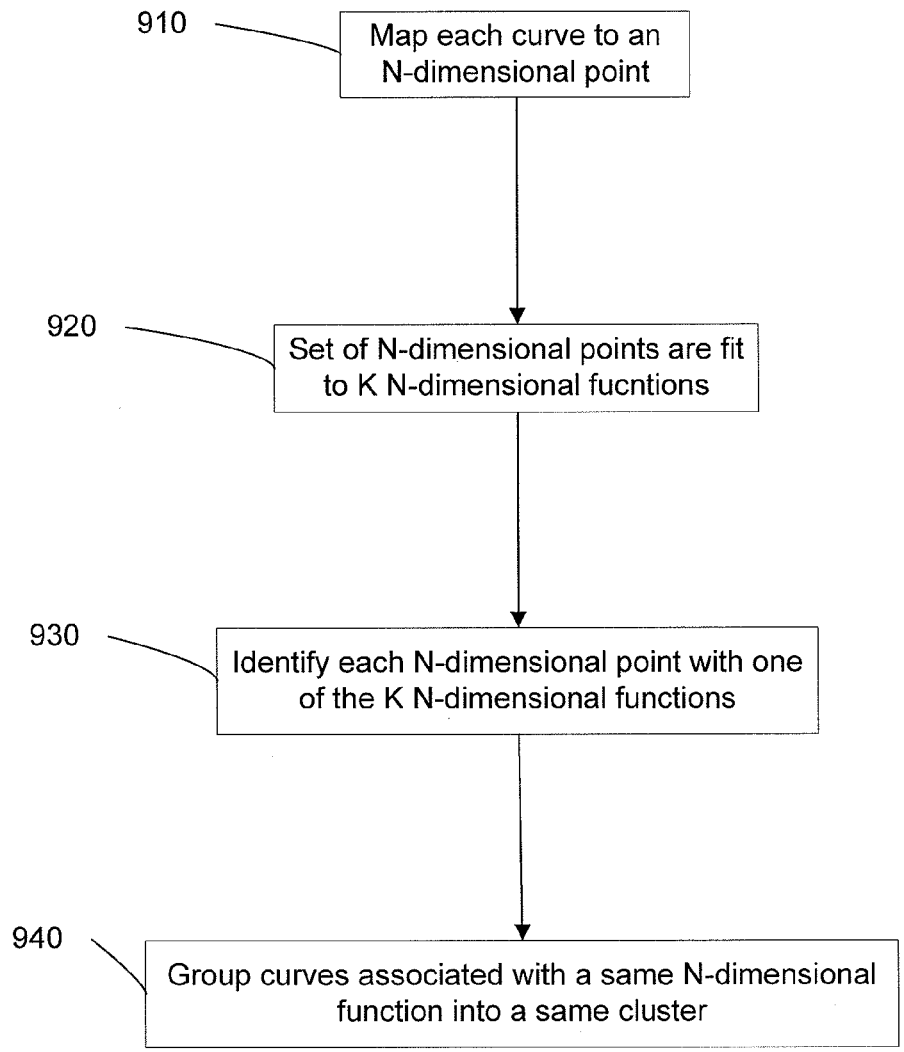
FIG. 9 is a flowchart illustrating a method 900 for analyzing the shapes of melt curves according to an embodiment of the present invention.

FIG. 9 is a flowchart illustrating a method 900 for analyzing the shapes of melt curves according to an embodiment of the present invention. In various embodiments, the melt curves may be the raw data received, be re-sampled, or be normalized in any of the methods mentioned herein. In one embodiment, method 900 may be used for the shape clustering of method 800.

In step 910, each curve is mapped to an N-dimensional point, where N is an integer greater than one. For example, for each curve, N values are calculated. In one aspect, each of the N values is an average of the reporter signal value for one of a plurality of segments of the melt curve. The set of N average values is then defined as a point in N-dimensional space.

In some embodiments, the segments of the curve are continuous and begin at the start of the melt region and end at the average threshold temperature. In other embodiments, the segments of the curve are continuous and begin at the start of the melt region and end at the end of the melt region.

In one embodiment, each melt curve is first RFU normalized and temperature shifted before being mapped to an N-dimensional point (e.g. N=7). The values of the N dimensions may be the average RFU values of each of the N contiguous and equal width windows starting at melt region start and ending at the average threshold temperature (e.g. as described in step 660).

In step 920, the set of N-dimensional points is fit to K N-dimensional functions. In one embodiment, these functions have a center, which can move during the fitting process. The centers may be initially placed such that the centers are far away from each other. The exact points may be chosen, e.g., to be on top of a data point. The functions are then moved and expanded to provide a better representation of the distribution of the N-dimensional data points.

This fitting may be done as part of an iterative application of a customized version of a clustering algorithm known as mixture of Gaussians. In such an embodiment, a given number (K) of N-dimensional Gaussian probability distributions is fit to the given set of N-dimensional points. The fitting algorithm maximizes the probability that the given set of points are from the K probability distributions by modifying the shape and location of each probability distribution until further modifications do not sufficiently improve the fit.

Each function can have the functional form of $e^{-C(X-X_0)^2}$, where X is an N dimensional point and $X_0$ is the center of the Gaussion. C is an exponential coefficient. In one embodiment, C is a series of different values for the polynomial in the coefficient. Since X is an N-dimensional point, C may be considered an N×N matrix of values. In one aspect, C is a symmetric matrix.

For each Gaussian function, points that are near to that function provide a greater contribution to the fit of the function. Thus, the overlap of the Gaussian with the data points is maximized. Ideally, the Gaussians stay separated so as not to significantly overlap with the same data points as another Gaussian predominantly overlaps.

In one embodiment, the coefficients C of the Gaussians can be constrained. For example, the K Gaussians' standard deviations (i.e. width) along each dimension, which is the diagonal elements of C, are forced to be within certain bounds. Some exemplary values for the bounds are: for 7-dimensional shape clusters, a maximum standard deviation for each dimension is 0.0065, and a minimum is 0.00075; and for the 1-dimensional melting temperature clusters, a maximum standard deviation is 0.7, and a minimum is 0.09.

In one aspect, these bounds roughly demarcate the expected amount of random variation in the melt curves. The datasets fed to this algorithm can be small (i.e. there are few points), and reasonable probability distributions can be difficult to derive. These bounds can make the results more stable and accurate, particularly on small datasets.

In another embodiment, the Gaussians can be forced to be axis aligned. In one aspect, the axis aligning is stabilizing and may be useful for small datasets. When a Gaussian is axis aligned, the values of $C_{ij}$ are equal to zero when i does not equal j, which are sometimes called the covariance. The values when i equals j (standard deviation of Gaussian width) may be non-zero.

In another embodiment, a K means algorithm is used instead of mixture of Gaussians. In this embodiment, a respective function is the mean of the points assigned to a particular cluster. Upon each iteration, a data point is assigned to the closest mean, and then a new mean is calculated, and the process repeats. In other embodiments, other clustering algorithms can be used.

Referring back to method 900, in step 930, each N-dimensional point is identified with one of the K N-dimensional functions. In one embodiment, a data point is identified with the function that is closest to that point. In another embodiment, the value of the function is used, with the function with the highest value being assigned the data point.

In step 940, the curves associated with a same N-dimensional function are grouped into the same cluster. As mentioned above, at least a portion of the sequences of a cluster can be identified as having a sequence variation.

Method 900 can depend upon how many N-dimensional functions are used. In other words, it can depend on the value of K, as used above. Embodiments can provide for methods of determining K.

Figure 10:
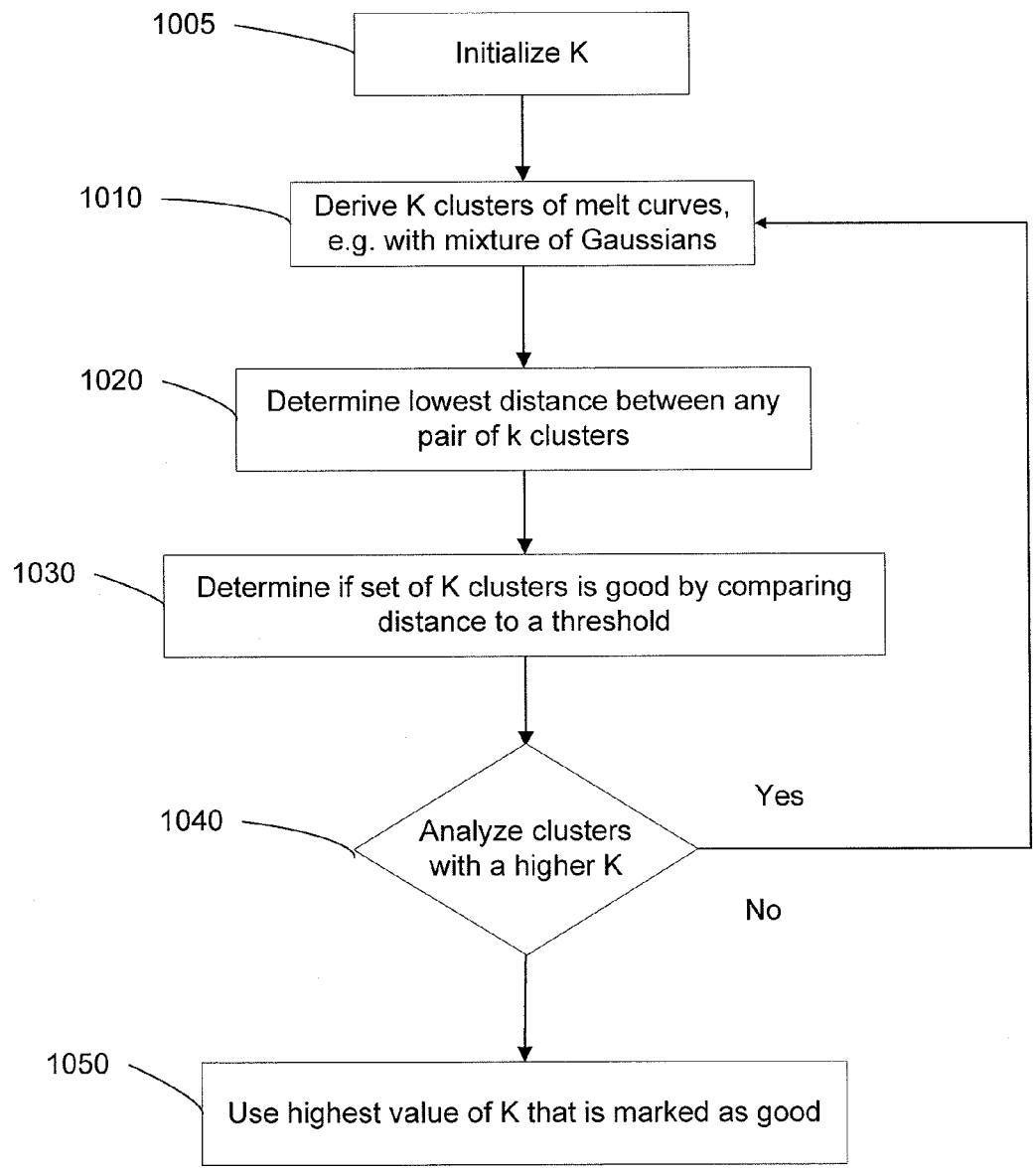
FIG. 10 is a flowchart of a method 1000 for determining the number of Gaussians or other functions to use for the clustering according to an embodiment of the present invention.

FIG. 10 is a flowchart of a method 1000 for determining a number of Gaussians or other functions to use for a clustering according to an embodiment of the present invention. In one aspect, an appropriate K to be used for the assignment of curves to a cluster is found by applying a clustering method (e.g. above described mixture of Gaussians) for multiple K.

In step 1005, the value of K is initialized to an integer (e.g. 2). In step 1010, K clusters are derived from a set of the N-dimensional points for each curve. For example, the above described method (e.g. using mixture of Gaussians algorithm) with the given K can be used to assign each data point to a cluster identified by which of the K probability distributions has the highest probability at that point.

In step 1020, a smallest distance between any pair of the K clusters is found. In one embodiment, the distance is a modified distance. The modified distance between a pair of clusters can be the Euclidean distance between the centroids of the pair of clusters D, multiplied by a scaling factor M. The scaling factor M can be based on the degree to which the standard deviations of the two clusters overlap, i.e. it is based on how distinct the clusters are. More distinct clusters provide an M which is greater than one, while less distinct clusters yield an M which is less than one. An effect of using the modified distance can be that clusters are allowed to be close to each other, if the points are compact with low noise (e.g. a low amount of overlap).

In one embodiment, the standard deviation coefficients C for the Gaussians (or any coefficient describing a width of a function) may be used to determine the overlap. In another embodiment, the value for the standard deviation of the spread of the points for a particular cluster may be determined as follows.

In deriving M, a pairwise cluster score CS can be first calculated:
stdDev1=the standard deviation of the points within cluster 1.
stdDev2=the standard deviation of the points within cluster 2.
avgStdDev=(stdDev1+stdDev2)/2
CS=D/avgStdDev
CS is a normalized quantity which does not depend on the scale of the data. In one embodiment, values of over roughly 3.5 indicate well differentiated clusters, while lower values indicate progressively undifferentiated clusters. In some embodiments, M is a non-linear function of CS in which M is greater than one for well differentiated clusters and less than one for undifferentiated clusters.

In one embodiment, the non-linear function of CS is derived from a set of hard-coded control points which are linearly interpolated between or extrapolated from. The following are the control points, in (CS, M) format: (−1, 0.1), (2.5, 0.1), (3.3, 1), (3.7, 1), (6.5, 2), and (100, 2).

In step 1030, if the modified distance M*D is greater than a certain threshold CD, then that set of K clusters is marked as "good". In one embodiment, CD is empirically derived, based on expected melt curve shape differences caused by heterozygous SNPs.

In step 1040, it is determined whether a new K is to be used. In one embodiment, this is determined based on whether the last K was marked as good. For example, if K is good then the process starting at step 1010 is then iterated with K+1. If K is bad, then no higher K values are analyzed. In another embodiment, a predetermined number of K are scanned. Thus, some K may be marked as bad, but the method can still analyze the results for a higher number K if the predetermined number has not been reached. In some instances, some lower K will be marked as bad, while a higher K is marked as good.

In step 1050, the K with the highest value that is marked as good is taken as the K to use for determining the clusters that the melt curves are to be assigned. The clusters can then be used to determine whether a sequence variation exists, as described herein.

In one embodiment, the determination of the K N-dimensional functions in step 1010 may be performed several times for a given K. Each time with a different starting point. In one aspect, if any of the iterations produce a good result, then the number K may be marked as good. In another aspect, whichever result is in the majority then that result is provided. A 50-50 split may be taken as bad or good.

Other embodiments, which can have improved robustness, combine hierarchical clustering concepts with the described methods. After finding some K clusters as described above, K−1 clusters can be found by merging the closest two of the K clusters. "Closest" can be in terms of absolute distance or modified distance, as described herein. That K−1 clustering is compared with the existing K−1 clustering, as found in the previous iteration of the loop (e.g. at step 1010 of previous iteration). If its "closest cluster distance" (described above) is greater than the existing K−1 clustering's "closest cluster distance", then it replaces the existing K−1 clusters. Thus, a new set of K−1 clusters may be determined, and this new set may be "good" whereas the old set may be "bad."

This "hierarchical clustering backtrack" can be used to find K−1, K−2, etc clusters. To find K−2 clusters, the hierarchical clustering for K−1 is hierarchically clustered in the same manner. In one embodiment, the backtracking may be stopped at a certain level (e.g. capped at K−2), whereas other embodiments may perform more backtracking.

Such backtracking can increase robustness by making the algorithm less susceptible to the starting points given to the clustering algorithm (e.g. the K-Means or mixture of Gaussians algorithms). For instance, if the points to be clustered are comprised of one large group of points with a non-zero standard deviation, along with a single outlier point, the algorithm should hopefully find those two clusters. If K-Means or mixture of Gaussians is told to find two clusters and is given the two most-distant points as start points, a local maxima will often be found in which one cluster contains the outlier and a few of the fringe points from the large group which are close to the outlier, while the other cluster contains the rest of the large group. However, if K-Means or mixture of Gaussians is told to find 3 or 4 clusters, chances are much greater that one of those clusters will be the single outlier, while the other clusters will be "closest to one another", especially in terms of modified distance, and thus will be merged in the hierarchical backtrack.

As described for method 900, the melt curves within each shape cluster may be partitioned into melting temperature clusters, e.g., as the sub-clusters from step 860. In one embodiment, the melting temperature clustering proceeds as shape clustering with the following modifications.

Each melt curve is mapped to a one-dimensional point. In one embodiment, that point is the melting temperature of the melt curve, which is derived by the standard means of discovering the peak location within the negative first derivative. In one aspect, the melt curve data used for this is the non-temperature shifted, RFU normalized data. In another embodiment, a threshold crossing (e.g. from step 650) within the RFU normalized data is used as the one-dimensional point.

In one embodiment, a specific modified distance threshold CD is used for the melt temperature clustering. Distance thresholds CD can be values which depend on a "clustering sensitivity setting" which can be changed by the user. Higher sensitivity yields lower distance thresholds. In some embodiments, shape clustering distance thresholds can range between 0.01 and 0.0565256. The melt temperature clustering distance thresholds can range between 0.05 and 1. Note that these values are in different units (RFU values (y axis) for shape clustering distance threshold, and temperature values (x axis) for the melt temperature clustering difference threshold).

VI. STR analysis

Besides SNP detection, embodiments are directed to short tandem repeat (STR) analysis. A short tandem repeat is a section of DNA which contains a number of repetitions of a certain short sequence. In human DNA, each person might have a different number of repetitions at any given STR site. Also, each person might have one number of repetitions in the DNA given to the person's mother, and a potentially different number of repetitions from the person's father. Thus, each site for a given individual can be encoded with two numbers, such as 3,5 if the mother gave 3 repetitions and the dad gave 5.

The STR sites can be isolated, amplified, and melted. The melt curve for a given person's DNA can have either one or two peaks in it, corresponding to their two numbers (two peaks if the numbers are different). Those peaks can be at different temperatures because longer strands of DNA melt at higher temperatures than shorter ones. The higher the number of repeats in the STR, the longer the strand.

One application of STR analysis is in DNA fingerprinting. There are international standards for STR sites which can be used to identify individuals. These sites are chosen for their random distribution of the different possibilities for the number of repetitions. With 10 or 15 such well-chosen sites, a person's "fingerprint", i.e. the 10 or 15 pairs of numbers, is very likely to be unique or at least very rare within a large population.

The STR analysis can be performed in a different manner than the SNP detection. One difference is in how the data fed to the clustering algorithm is calculated. For example, which aspect of the melt curve data is used and how the data is normalized. Method 600 of normalization can work well for SNP detection because, in SNP detection, the x-axis distance between the start and end regions is small (usually less than five degrees). This small value of the x-axis distance can be because the product in all the wells of interest melts at nearly the same temperature. There is typically very little noise between the start and end regions, only melt transitions, which are the data of interest. This typically does not hold true for STR analysis. For some samples, there will be a large temperature span (e.g. 35 degrees) between the start region and the point at which the product starts to melt.

Figure 11:
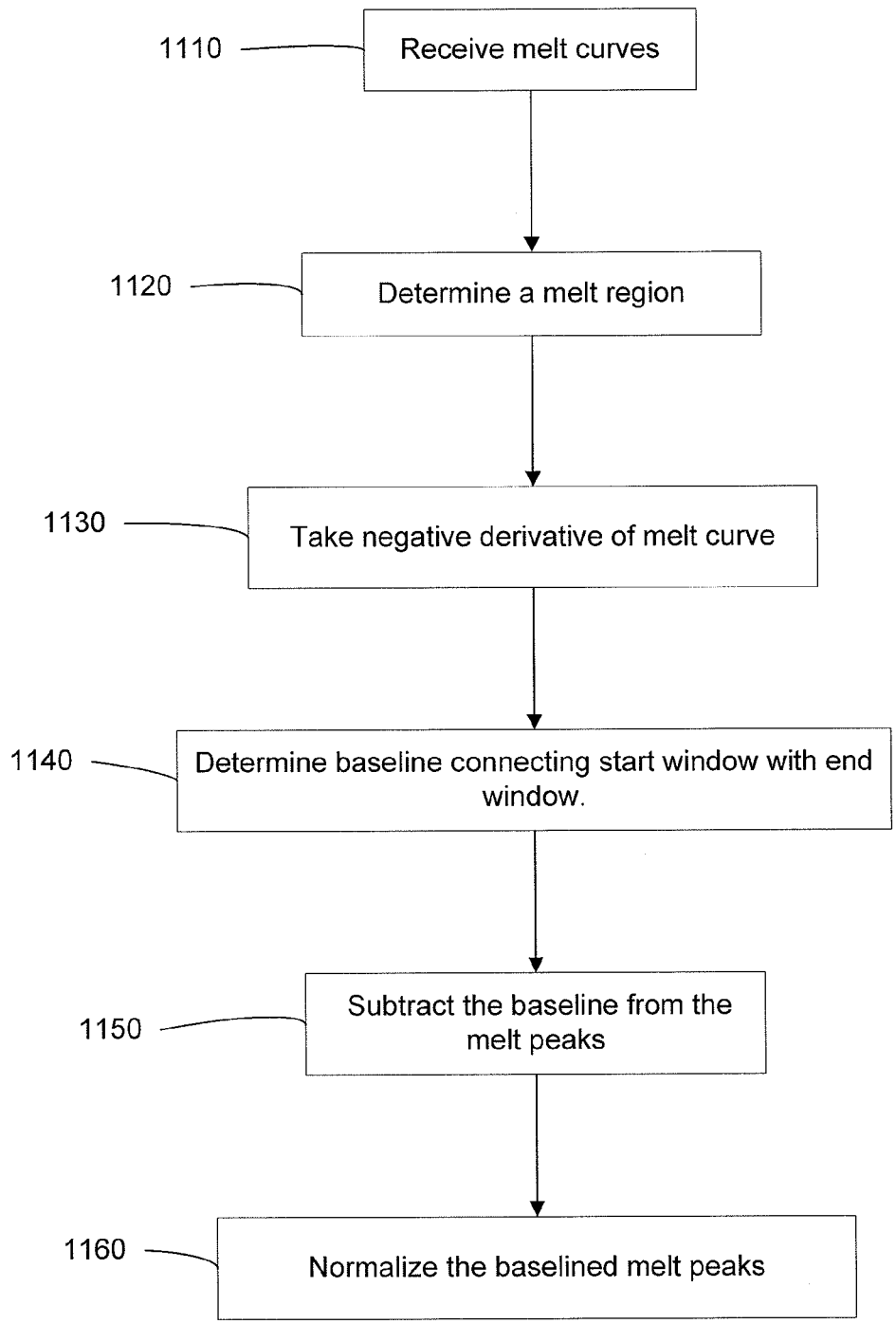
FIG. 11 is a flowchart illustrating a method 1100 of pre-processing melt curve data for clustering according to embodiments of the present invention.

FIG. 11 is a flowchart illustrating a method 1100 of preprocessing melt curve data for clustering according to embodiments of the present invention. Rather than starting with the raw melt curves as in SNP detection, STR detection can start with the "melt peaks.", which are the negative first derivative of the melt curves. In one embodiment, method 1200 can be used to for step 240 in method 200.

In step 1110, melt curve data is received. In step 1120, a melt region is determined. In one embodiment, the start and end regions can be positioned at approximately 25 degrees and 60 degrees to encompass all melt transitions for a specific set of the samples. In an STR analysis, a large amount of noise can be between the start region and the melt transition, and again between the melt transition and the end region. If method 600 was used to normalize the data, there could be large differences between the samples because the relatively minor differences outside their melt regions can be effectively amplified by the normalization scaling In step 1130, negative derivative data of the melt curves is taken. The negative derivative data (melt peak data) can be used rather than the raw melt curve. FIG. 12A shows melt peak curves according to an embodiment of the present invention. In one embodiment, the melting temperature is considered to be the temperature (x-axis position) of the tip of the melt peak, i.e., the inflection point of the melt curve, the point at which the DNA product is melting the fastest. Melt peak data typically starts low and ends low, with one or more peaks in the middle (depending on how many different products were in the well).

In step 1140, a baseline is created which connects the melt peak data at the start region with the melt peak data at the end region. FIG. 12B shows a plot of the baseline of the melt peak curves in FIG. 12A. In one embodiment, the baseline connects the start of the melt region to the end of the melt region. In another embodiment, other points in the start region (e.g., besides the end of the start region) are connected to other points in the end region (e.g. besides the start of the end region).

In step 1150, the baseline is subtracted out from the melt peaks. In one embodiment, negative values are floored at 0. FIG. 12C shows the resulting data from subtracting out the baseline shown in FIG. 12B.

In step 1160, the baselined melt peaks are normalized such that their maximum value between the start and end regions is 1, and the minimum value is zero. The normalized baselined peaks can then be clustered. In one embodiment, the baselined melt peak can each be converted into a plurality of N-dimensional points, e.g., one point for each segment of the melt peak curve. In one aspect, the segments can start at a point where the melt peak curves become non-zero and end at the end of the melt region.

In performing shape clustering for STR analysis, the N-dimensional points can be different from the N-dimensional points for the SNP analysis. For reference, in SNP detection, the N-dimensional "shape point" can be the average RFU values of each of the N contiguous and equal width windows starting at melt region start and ending at the average threshold temperature (e.g. as described in step 660). For the STR analysis, rather than ending at the average threshold temperature, the N-dimensional "shape point" can end at the melt region end window. As noted above, in one embodiment, no temperature shifting is done in STR detection processing so there is no average threshold temperature. Also, rather than N=7, as can be used for SNP detection, STR detection can use N=30, to get enough resolution to catch peaks that occur anywhere throughout the range between begin and end window. In another embodiment, melt temperature clustering is not performed for STR analysis.

Figure 13:
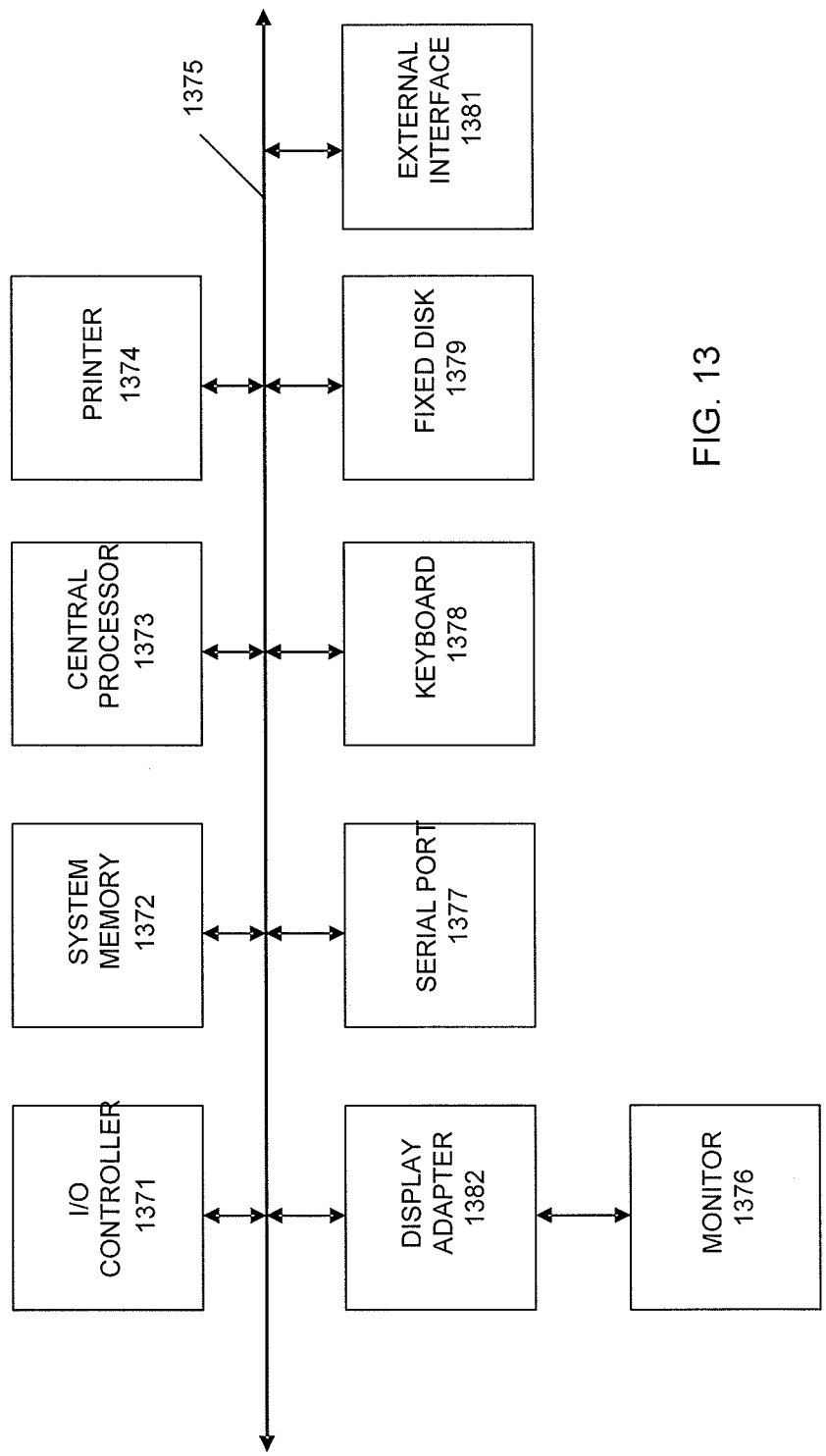
FIG. 13 shows a block diagram of an exemplary computer apparatus usable with system and methods according to embodiments of the present invention.

FIG. 13 shows a block diagram of an exemplary computer apparatus usable with system and methods according to embodiments of the present invention.

Any of the PLC or computer terminal may utilize any suitable number of subsystems. Examples of such subsystems or components are shown in FIG. 13. The subsystems shown in FIG. 13 are interconnected via a system bus 1375. Additional subsystems such as a printer 1374, keyboard 1378, fixed disk 1379, monitor 1376, which is coupled to display adapter 1382, and others are shown. Peripherals and input/output (I/O) devices, which couple to I/O controller 1371, can be connected to the computer system by any number of means known in the art, such as serial port 1377. For example, serial port 1377 or external interface 1381 can be used to connect the computer apparatus to a wide area network such as the Internet, a mouse input device, or a scanner. The interconnection via system bus allows the central processor 1373 to communicate with each subsystem and to control the execution of instructions from system memory 1372 or the fixed disk 1379, as well as the exchange of information between subsystems. The system memory 1372 and/or the fixed disk 1379 may embody a computer readable medium.

The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method of identifying a sequence variation between nucleotide sequences, the method comprising:
    receiving a plurality of sets of data points, each set corresponding to a different sample that contains copies of a double stranded molecule of two nucleotide sequences, each data point of a set including a signal value and a temperature value for the sample where the temperature increases for each successive data point, wherein each set defines a melt curve;
    at least one processor determining a melt region for the melt curves by:
        for each melt curve:
            taking a second derivative;
            identifying start and end temperatures where a function of the second derivative crosses a boundary threshold value;
        based on the respective start temperatures of the melt curves, identifying a melt region start;
        based on the respective end temperatures of the melt curves, identifying a melt region end;
    assigning each melt curve to a respective cluster, wherein the melt curves assigned to a same cluster have one or more similar properties in the melt region relative to melt curves in other clusters; and
    identifying at least a portion of the nucleotide sequences corresponding to at least one cluster as having a sequence variation relative to the nucleotide sequences of another cluster.

2. The method of claim 1, wherein identifying the melt region start includes identifying a respective start temperature that is greater than a predetermined amount of other start temperatures as the melt region start, and wherein identifying the melt region end includes identifying a respective end temperature that is less than a predetermined amount of other end temperatures as the melt region end.

3. The method of claim 2, wherein the predetermined amount of other start temperatures is a percentage.

4. The method of claim 1, wherein the double stranded molecule is a gene.

5. The method of claim 4, wherein each sample contains a same gene from different organisms.

6. The method of claim 4, wherein the sequence variation is a mutation.

7. The method of claim 1, wherein the function of the second derivative is a moving average of the second derivative.

8. The method of claim 1, further comprising:
    prior to assigning the melt curves to clusters, normalizing each melt curve by:
        offsetting the data points of each melt curve so that points within an end region have an average value of a first value, wherein the end region is a predetermined temperature range starting at the melt region end; and
        multiplying the melt curve by a number such that the data points in a start region have an average value of a second value, wherein the start region is a predetermined temperature range ending at the melt region start.

9. The method of claim 8, wherein the first value is zero and the second value is one.

10. The method of claim 1, further comprising:
    for each melt curve, identifying a threshold temperature at which the melt curve crosses a threshold;

calculating an average threshold temperature from the respective threshold temperatures;

shifting each melt curve so that the melt curve crosses the threshold at the average threshold temperature;

performing a second normalization of each melt curve includes:

modifying the data points of the melt curve having a lower temperature than the average threshold temperature such that the data points in the start region have an average value of a third value.

11. The method of claim 10, wherein performing a second normalization of each melt curve further includes:

modifying the data points of the melt curve having a higher temperature than the average threshold temperature such that the data points of the melt curve have a value of the threshold at the average threshold temperature and an average value of a fourth value in the end region.

12. The method of claim 10, wherein the second value is the same as the third value.

13. The method of claim 1, further comprising:

at least one processor selecting a cluster of melt curves;

the at least one processor determining a melting temperature of each melt curve of the selected cluster;

the at least one processor grouping the melt curves of the selected cluster into a plurality sub-clusters based on the respective melting temperatures; and identifying at least a portion of the nucleotide sequences corresponding to at least one sub-cluster as having a sequence variation relative to the nucleotide sequences of another sub-cluster.

14. The method of claim 13, wherein the nucleotide sequences of the at least one sub-cluster are identified as having a homozygous mutation.

15. The method of claim 1, wherein the at least one processor assigns each melt curve to a respective cluster by analyzing shapes of the melt curves, wherein the melt curves assigned to a same cluster have one or more similar shape properties in the melt region relative to melt curves in other clusters, wherein analyzing shapes includes:

for each melt curve:

calculating N average values, each value the average of one of a plurality of continuous segments of the melt curve;

defining the set of N average values as a point in N-dimensional space;

fitting the N-dimensional points to K N-dimensional functions;

identifying each N-dimensional point with one of the K N-dimensional functions; and grouping the melt curves associated with a same N-dimensional function into a same cluster.

16. The method of claim 15, further comprising identifying a value for K by:

clustering the melt curves for a plurality of K values;

for each set of K clusters:

determining a distance between each of the clusters of the set;

if each of the distances is greater than a threshold CD, then the set of K clusters is marked as good;

determining the highest value for K for which the clusters are marked as good; and using the clusters resulting from the clustering for the highest value of K to identify the sequence variation.

17. The method of claim 15, wherein the N-dimensional functions are Gaussian functions.

18. The method of claim 17, wherein the width of the Gaussians are constrained to be within a predetermined range.

19. The method of claim 15, wherein the N-dimensional functions are each a function that computes an average of data points assigned to a respective function.

20. The method of claim 1, further comprising:

The at least one processor taking a negative first derivative of each melt curve to determine respective melt peak curves, wherein the at least one processor assigns each melt curve to a respective cluster, wherein the melt curves assigned to a same cluster have one or more similar properties for the melt peak curves in the melt region relative to melt curves in other clusters.

21. The method of claim 20, further comprising:

determining a baseline of each of the negative first derivatives, wherein baseline connects the melt region start to the melt region end; and subtracting the baseline from the respective melt peak curves to provide respective baselined melt peak curves, wherein the melt curves assigned to a same cluster have one or more similar properties for the respective baselined melt peak curves in the melt region relative to melt curves in other clusters.

22. The method of claim 21, wherein negative data points of a baselined melt peak curve are set to zero.

23. The method of claim 22, wherein the respective baselined melt peak curves are normalized before clustering, wherein the normalization includes modifying the data points of the baselined melt peak curves such that their maximum value between the start and end regions is 1, and the minimum value is zero.

24. A computer product comprising a non-transitory computer readable medium storing a plurality of instructions that when executed control a computer system to identify a sequence variation between nucleotide sequences, the instructions comprising:

receiving a plurality of sets of data points, each set corresponding to a different sample that contains copies of a double stranded molecule of two nucleotide sequences, each data point of a set including a signal value and a temperature value for the sample where the temperature increases for each successive data point, wherein each set defines a melt curve;

at least one processor determining a melt region for the melt curves by:

for each melt curve:

taking a second derivative;

identifying start and end temperatures where a function of the second derivative crosses a boundary threshold value;

based on the respective start temperatures of the melt curves, identifying a melt region start;

based on the respective end temperatures of the melt curves, identifying a melt region end;

assigning each melt curve to a respective cluster, wherein the melt curves assigned to a same cluster have one or more similar properties in the melt region relative to melt curves in other clusters; and identifying at least a portion of the nucleotide sequences corresponding to at least one cluster as having a sequence variation relative to the nucleotide sequences of another cluster.

* * * * *